United States Patent [19]

Hatschek et al.

[11] Patent Number: 5,489,515
[45] Date of Patent: Feb. 6, 1996

[54] DEVICE FOR ANALYZING THE METABOLISM OF CELLS

[75] Inventors: Rudolf Hatschek, Fribourg; Erich W. F. Heitz, Schaffhausen, both of Switzerland

[73] Assignee: AVL Medical Instruments AG, Schaffhausen, Switzerland

[21] Appl. No.: 353,268

[22] Filed: Dec. 5, 1994

[30] Foreign Application Priority Data

Dec. 9, 1993 [EP] European Pat. Off. .............. 93810866

[51] Int. Cl.$^6$ .............................. C12Q 1/02; G01N 27/00
[52] U.S. Cl. .............................. 435/29; 435/817; 204/403
[58] Field of Search .............................. 435/4, 29, 817, 435/973; 436/806; 204/153.12, 153.21, 403

[56] References Cited

U.S. PATENT DOCUMENTS 4,591,550  5/1986  Hafeman ..................... 435/4
4,915,812  4/1990  Parce ......................... 204/403

OTHER PUBLICATIONS

Parce J., Detection of Cell–Affecting Agents . . . Science 246 (1989) pp. 243–247.
Owicki J., Continuous Monitoring of Receptor . . . Proc Natl Acad Sci 87 (1990) pp. 4007–4011.
Owicki J., Biosensors Based on the Energy Metabolism . . . Bioscensors & Bioelectronics 7 (1992) 255–272.
Grattarola M., On–Like Extra Cellular pH . . . STN Pharma Sciences (1993) 3 (1) pp. 31–34.

*Primary Examiner*—Ralph J. Gitomer
*Attorney, Agent, or Firm*—Watson, Cole, Grindle & Watson

[57] ABSTRACT

A device for analyzing the metabolism of cells includes a supporting base which carries a pH measuring electrode, a control electrode designed for proton exchange with the liquid, a reference electrode, and a counterelectrode, and which, together with at least one other part, confines a hollow space containing the cells and a liquid. The electrodes are connected to electronic circuit elements. In the course of an analysis the pH value of the liquid is determined by means of the pH measuring electrode and the reference electrode. Between the control electrode and the counterelectrode an electric current is passed through the liquid and controlled such that the pH of the liquid is maintained at a constant preset value beneficial to the cells, by proton exchange with the control electrode. In addition, the amount of charge required for generating the current during the measuring period is determined to obtain a measure for the intensity of the metabolic process and thus for the vitality of the cells.

11 Claims, 1 Drawing Sheet

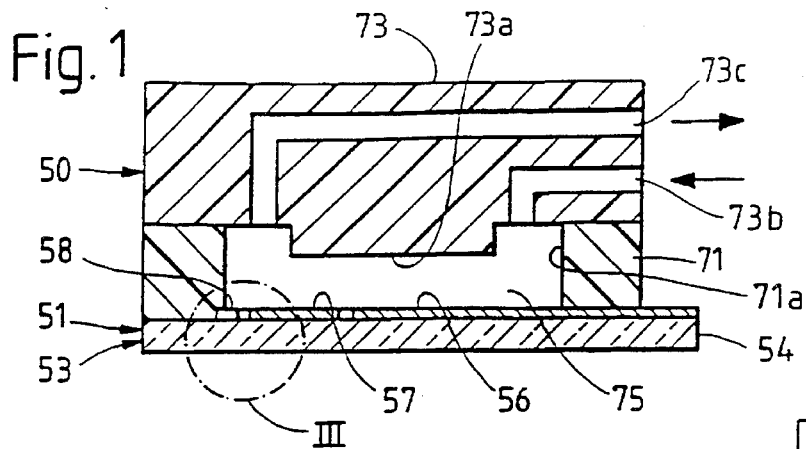
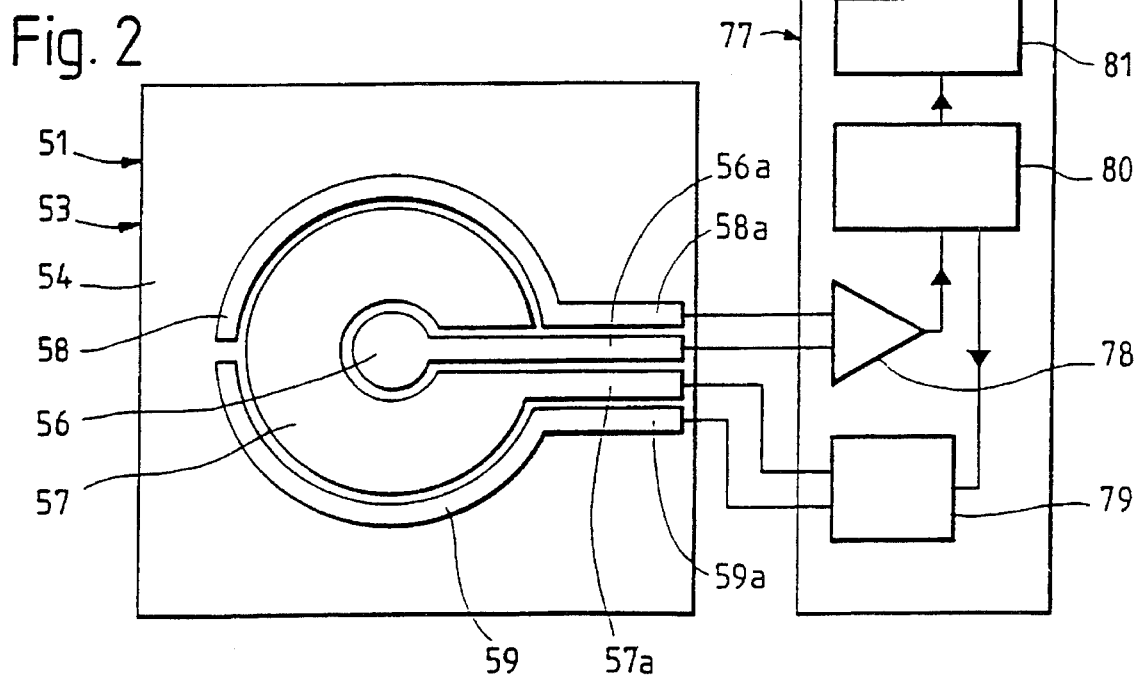
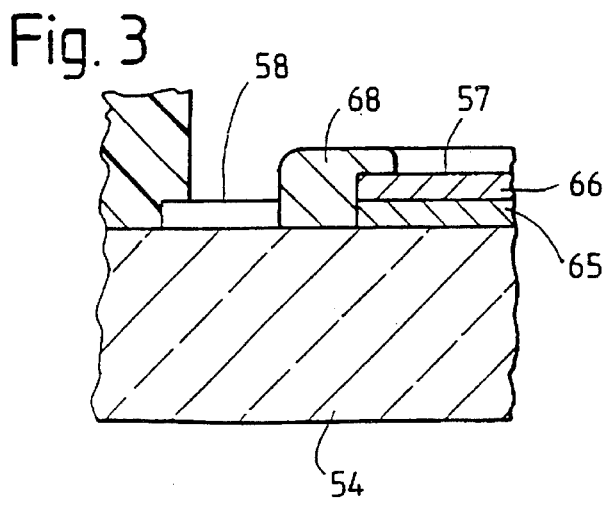
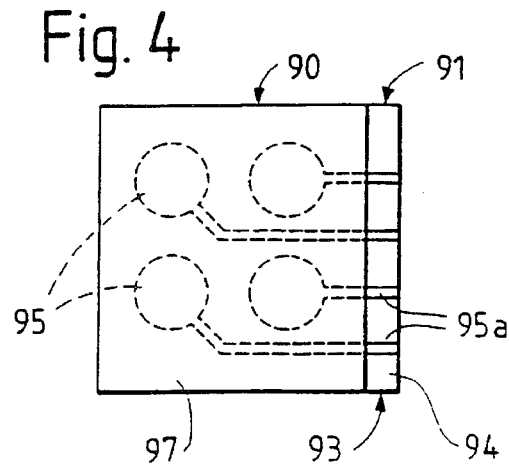

DEVICE FOR ANALYZING THE METABOLISM OF CELLS

BACKGROUND OF THE INVENTION

The invention relates to a device for analyzing the metabolism of cells that border on a liquid.

The cells may be microorganisms or other living cells which were taken or in some way derived from a human, animal or vegetable organism. An aqueous nutrient solution may be used as a liquid. During investigation of the cell metabolism the cells may release protons into the adjacent liquid by one or more metabolic processes. The release of protons may be either direct, or the cells may give off substances into the liquid which will then release protons by dissociation. In many metabolic processes the cells will produce carbon dioxide, for example, which will then form carbonic acid in the liquid surrounding the cells. Besides, low-molecular, aliphatic hydroxy acids, such as lactic acid, may be generated in the cells, which are delivered to the liquid through the cell membrane. It goes without saying that the protons originally present in the liquid and/or released during the investigation are attached, at least partly, to water molecules in the usual manner.

DESCRIPTION OF THE PRIOR ART

In the publications "Light-Addressable Potentiometric Sensor for Biochemical Systems" by Dean G. Hafeman, J. Wallace Parce, Harden M. McConnel, Science, Vol. 240, 1988, pp. 1182–1185, and "Silicon Micromachining in the Fabrication of Biosensors Using Living Cells" by Luc J. Bousse, J. Wallace Parce, John C. Owicki, and Karen M. Kercso, Tech. Dig. IEEE Solid State Sensor Workshop, 1990, pp. 173–176, reference is made to devices for studying the metabolism of living cells, which are provided with a chamber for receiving the cells and an aqueous liquid. The devices are further provided with sensing means for determining the pH value of the liquid. The sensing means have a silicon semiconductor sensor whose surface, which is adjacent to the liquid during the measurement process, is formed by an electrically-insulating layer of silicon hydroxynitride or silicon nitride. The sensing means are further provided with at least one light diode for illuminating the sensor, and at least one electrode dipping into the liquid, in order to generate a difference in potential between the liquid and the sensor. In the course of the measurement a nutrient liquid is passed through the chamber intermittently and the photocurrent which is generated by the sensor each time the liquid flow is interrupted, is measured. The result obtained is a measure for the change in pH produced by the cell metabolism, and thus for the metabolism itself.

Many cells are sensitive to changes in the pH value of the ambient liquid, however. Since the known devices are characterized by a change in pH during the period of measurement, they suffer from the disadvantage that the pH value of the liquid is not well suited for the cells during a large part of the measuring period.

The carbonic acid generated in the liquid surrounding the cells during a number of metabolic processes, partly dissociates into protons and bicarbonate. Together with the non-dissociated carbonic acid, the bicarbonate may act as a buffer, reduce the change in pH and distort the measured result.

Another disadvantage of the known devices is that the sensing means require a comparatively large number of different components for pH measurement, i.e., at least one light diode and at least one electrode in addition to the silicon sensor.

In "Preparation of Iridium Oxide and its Application in Sensor-Actuator Systems" by W. Olthuis, J. C. van Kerkhof, P. Berveld, M. Bos, W. E. van der Linden, Sensors and Actuators B. 4, 1991, pp. 151–156, Elsevier Sequoia, an apparatus for coulometric titration is disclosed that includes a body provided with a layer of iridium oxide, which is used as an electrode for donating and accepting hydrogen ions. The publication does not refer to the device as a possible instrument for investigating the metabolism of cells. As the pH value will change during titration, this kind of measuring process, if used for studying cell metabolism—in analogy to the measurement of pH change described in the publications by Hafeman et al., and Bousse et al. mentioned above —would suffer from the drawback that the ambient liquid surrounding the cells does not have its optimum pH value during the measurement period.

As has been shown by our own studies and investigations, the fabrication of iridium oxide layers according to the methods described in the above publication by Olthuis et al. will give polycrystalline, dark, and largely opaque oxide layers. If used for proton exchange or pH measurement, such layers of iridium oxide have additional disadvantages: their proton exchange rate and measuring sensitivity are subject to relatively strong changes, and they are not suited for devices requiring a transparent oxide layer for additional microscopic or optical measurements.

SUMMARY OF THE INVENTION

It is an object of the invention to provide a device for analyzing the metabolism of cells which avoids the disadvantages of the known devices and which permits the amount of protons released in the liquid during at least one metabolic process to be determined while avoiding changes in the pH value of the liquid in a manner not beneficial to the cells during the measuring process. An additional aim is to enable measurement to be performed very quickly if so desired.

According to the invention the device includes a pH sensing means for measuring the pH value of the liquid with bordering cells, a control electrode for proton exchange with the liquid, a counterelectrode in contact with the liquid, and electronic circuit elements connected to the pH sensing means, the control electrode and the counterelectrode for (a) generating a current in the liquid between the control electrode and the counterelectrode such that, via proton exchange with the control electrode, a desired preset pH value in the liquid will be provided, and (b) measuring the current (or a variable associated therewith) to determine the intensity of cell metabolism.

For the purpose of study the cells may be immobilized on a surface of the device and may be exposed to the liquid at least in those areas that are neither in contact with the surface of the device nor adjacent to other cells. The cells could also be partly or totally suspended in the liquid, however. The liquid may thus essentially surround the cells.

During the use of the device of the invention the pH sensing means, the control electrode configured as a proton donor and/or acceptor for the purpose of proton exchange, and the counterelectrode can be brought into contact with the liquid. Moreover, the pH sensing means can be used for determining the pH value of the liquid. By means of the electronic circuit elements an electric current may be generated which flows through the liquid from the control electrode towards the counterelectrode and/or vice versa, inducing the control electrode to exchange protons with the liquid, i.e., to release or acquire protons depending on the flow direction. The circuit elements are capable of regulating the current such that the pH value will equal a preset value. The circuit elements will also serve to determine the electric current flowing through the liquid and/or a measurement variable associated with this current.

The preset value to which the pH value is adjusted during analysis or measurement may be constant and equal to the optimum value for the cells under inspection at least for one given measuring period. It should be noted that the optimum pH value may differ for different types of cells. For this reason the device may be provided with manually-adjustable controls for manually setting a desired value corresponding to the optimum pH value of a particular type of cells to be analyzed.

In a preferred embodiment of the invention the circuit elements are used not only for automatically regulating the intensity of the electric current flowing through the liquid, but also for automatically controlling its direction, permitting the control electrode to release or accept protons as required. Manually adjustable controls may be provided by means of which the direction of the current can be adjusted either manually or automatically.

The electric current passed through the liquid for the purpose of pH adjustment provides a measure for the amount and number of protons released and/or dissociated in the liquid by the cells per unit time, and is proportional to the rate of released and/or dissociated protons if the pH value has been adjusted to a constant set value.

The device may be configured so as to set a starting point of a measurement period and the duration of a measuring and/or integration period with the use of one or more manually-operated actuating elements and/or with automatically-operated circuit elements. The circuit elements may be configured so as to integrate the intensity of the electric current flowing through the liquid during the measuring and/or integration period.

If the instantaneous pH value fluctuates about the desired value during the control process, and if the direction of the current changes accordingly, the current intensity may be given a positive or negative sign upon integration, depending on the direction of the current. The integral will provide a measure for the electric charge making up the current during the measuring and/or integration period, and for the amount of protons released and/or dissociated by the cells.

The pH sensing means of the device, which are used for pH measurement, preferably comprise a pH measuring electrode, which is in contact with the liquid adjacent to the cells for the time of analysis, and whose electric potential vis-a-vis the liquid is dependent on the pH value of the liquid. The pH sensing means preferably further comprise a reference electrode whose electric potential vis-a-vis the liquid is at least essentially independent of the pH value, and will either remain constant upon a change in pH or undergo a change that is considerably smaller than that of the potential of the pH measuring electrode.

The device preferably is provided with a supporting base designed for carrying the electrodes referred to above, with an electrically insulating part. The insulating part may be configured as a single-piece, essentially plane plate of crystalline material, such as aluminum oxide, i.e., a piece of a synthetic, transparent, colorless sapphire. The insulting part has a level surface, for example, on which electrically conductive or semi-conductive layers separated by spaces are applied, which layers form the above electrodes or at least their free surface areas which are brought into contact with the liquid during analysis.

The pH measuring electrode and the control electrode preferably have a layer of one or more metal oxides, which forms their free surface bordering on the liquid during measurement. This metal oxide layer should be reasonably conductive or at least semi-conductive.

The metal oxide layer of the pH measuring electrode and the control electrode preferably is made of one or more oxides of iridium or palladium. The metal oxide layer of the control electrode may consist of at least one oxide of at least one of the metals zirconium, niobium, rhodium, tantalum, rhenium, platinum. The oxide layer preferably consists of an oxide or oxides of only one of the metals listed above.

A layer consisting of iridium oxide is particularly well suited as a proton donor and/or acceptor for use as a control electrode, and also for a pH measuring electrode, as it will require only a small electric electrode potential for proton exchange. This potential is below the potential at which any chlorine ions in the liquid are oxidized, for instance. Moreover, in an electrode comprising a layer of iridium oxide the electrode potential necessary for proton exchange is smaller than the potential effecting the electrolysis of water. A layer consisting of palladium oxide is also acceptable for use as a control electrode serving for proton exchange, and a pH measuring electrode.

If the oxide layer of the control electrode and the pH measuring electrode consists of an oxide of a metal with several oxidation numbers, it is proposed that at least that part of the oxide layer which forms the free surface of the oxide layer and is adjacent to the liquid during analysis, should consist of the oxide of the highest possible oxidation number. This will protect the oxide layer against further oxidation, thus contributing to the chemical stability of the oxide layer. In the instance of a layer of iridium oxide, this means that at least the part forming its free surface consists of the oxide of the highest oxidation number, i.e., $IrO_2$.

The electrically-insulating part is provided with a coating or intermediate layer, preferably between the part itself and the semi-conductive metal oxide layer forming part of the pH measuring electrode or control electrode, which intermediate layer is configured as an electrically conductive metal layer. This metal layer consists of the metal or metals whose oxide or oxides form the metal oxide layer. Between a region which is formed by an oxide layer of the highest oxidation number and faces away from the intermediate layer, and the metal layer, the metal oxide layer may have a transition region adjacent to the metal layer, which region consists of an oxide of a low oxidation number.

If the metal oxide layer of the pH measuring electrode and/or the control electrode consists of iridium oxide, the preferably existing metal layer may consist of iridium. In this instance the oxide layer may have yet another region, which consists of $Ir_2O_3$ and is situated between a region of $IrO_2$ provided on its surface, and the metal layer consisting of iridium.

In a preferred variant of the device of the invention the metal oxide layer of the pH measuring electrode and/or the control electrode, or at least that part of the respective metal oxide layer which constitutes the free surface area of the electrode(s) that is in contact with the liquid during the period of measurement and analysis, is monocrystalline. Such a monocrystalline metal oxide layer has a stable structure. Moreover, unlike a polycrystalline oxide layer, it has no interior interfaces. In this manner a compact oxide layer is obtained which is entirely free of cracks and microfissures and will remain that way if used appropriately. When the monocrystalline metal oxide layer is exposed to the liquid during operation, the liquid cannot penetrate the metal oxide layer. Due to these properties the electrode provided with a monocrystalline metal oxide layer is characterized by a stable, easily reproducible behavior in both short-term and long-term tests to be discussed in greater detail later on.

The reference electrode which, together with pH measuring electrodes, is used for pH measurement, may consist, at least partly, of silver chloride or calomel, and may have a layer of silver chloride or calomel, which is applied on the insulating part referred to above, and is brought into contact with the liquid during testing.

The counterelectrode which, together with the control electrode, is used for generating an electric current flowing through the liquid, may consist, at least partly, of metallic material and may be provided with a metal layer on the insulating part referred to above.

In an advantageous embodiment of the device the insulating part configured as a small plate, together with at least one other part, will bound a cavity receiving the cells and the liquid, adjacent to which the electrodes are placed. This cavity preferably is a free, i.e., empty hollow space which does not contain any solid material and is sealed against its environment on all sides. The electrodes may be located close to one another and may be rather small, for example enveloped by a circle or square whose diameter or side does not exceed 10 mm or even 5 mm. The maximum height of the hollow space measured at a right angle relative to the surface of the base carrying the electrodes, may be 3 mm preferably, or even only 1 mm, approximately. This configuration and dimensioning of the device will enable comparatively small amounts of cells and liquids to be analyzed. Furthermore, the amount of protons released and/or dissociated by the cells in the liquid may be measured with satisfactory accuracy within a short measurement period. For instance, the proton amount may be determined in a measurement period of 30 seconds maximum or even 10 seconds maximum.

The monocrystalline metal oxide layer may be prepared and simultaneously applied on the base by high-vacuum, thin-layer techniques. With such technologies the oxide layer is preferably deposited on a surface formed by a metallic layer on the support. For preparation of an iridium layer, for example, iridium is evaporated in a first step onto an electrically insulating, heat-resistant (at least up to 800° C.) substrate which may be configured as a sapphire plate, until a metallic layer of pure iridium has built up. In a second step following immediately afterwards, more iridium may be evaporated onto the metallic layer deposited during the first step while oxygen is introduced into the chamber containing the substrate. During that second step the substrate may be heated to at least 600°–800° C. In the course of this process a monocrystalline iridium oxide layer will build upon the metallic layer. Similarly, monocrystalline metal oxide layers may be obtained from any of the other metals referred to above.

If an electrically-insulating substrate carries a reference electrode of silver chloride and/or a counterelectrode of platinum in addition to one or more electrodes provided with a metal oxide layer, additional silver and/or platinum may be evaporated onto the substrate, and the silver may later be converted into silver chloride. Similarly, strip conductors may be evaporated onto the substrate, which are electrically connected to the individual electrodes. In this manner a substrate carrying several electrodes is prepared at comparatively low cost.

The metal oxide layer could also be deposited on a metallic layer which is not prepared by vapor deposition but with the use of some other technique. Furthermore, the oxide layer might be prepared by growing an oxide monocrystal which is subsequently cut and/or polished. The small plate obtained in this way may then be attached to the base.

In an advantageous embodiment of the device of the invention the metal oxide layer has a thickness of 50 nm minimum and 1 mm maximum. If the oxide layer is prepared by thin-layer technologies, its thickness may amount to 1,000 nm, for instance. For a metal oxide layer forming part of a pH measuring electrode, a thickness of 100–300 nm is recommended. Such a relatively small thickness will permit rapid measurements. For a metal oxide layer forming part of a control electrode, a greater thickness is recommended to enable the layer to release or accept sufficient amounts of protons. In such cases the oxide layer may have a thickness of at least 300 nm up to some 600 nm or more. If a metal oxide layer is to be transparent it is recommended that the thickness of the oxide layer should not exceed 300 nm to minimize light absorption.

A metal oxide layer forming part of the control electrode and/or pH measuring electrode could be polycrystalline instead of monocrystalline.

Instead of a metal oxide layer the pH measuring electrode and/or the control electrode could also have a layer which consists, at least partly, of platinum.

Moreover, instead of a pH measuring electrode, the pH sensing means could be provided with a pH silicon semiconductor sensor or detector with a layer of doped silicon and a layer of silicon nitride or silicon oxide nitride. In such cases the sensor configuration could be similar to that of the sensors described in the publications of Hafeman et al., and Bousse et al. cited at the beginning of this paper. The reference electrode may be replaced by one or more electrodes performing the functions of the electrodes known from the above publications.

Prior to measuring the amount of proton released by the cells, an electrolytic liquid consisting of an aqueous solution may be provided. This liquid should have an optimum pH value for the cells to be investigated, and a low buffering capacity—or none at all—before it enters into contact with the cells. If the buffering capacity is small or entirely absent, the amount of protons released by the cells during measurement may be determined quickly and accurately.

The watery liquid adjacent to the cells and essentially surrounding them during an investigation may contain at least one nutrient initially, such as glucose and/or glutamine. In addition, it may contain at least one additive essential to cell growth, and usually several such additives, such as vitamins, amino acids, salts, nucleosides, hormones, or exogenous growth factors. The liquid may further contain at least one dissolved gas, such as oxygen and/or carbon dioxide.

Furthermore, one or more test substances may be added to the liquid, whose effects on the cells are to be investigated. Suitable test substances include pharmaceutical agents or environmental pollutants.

In the course of analysis the amount of acid or acids released into the liquid by microorganisms or other cells during one or more metabolic processes may be measured by electroanalytic techniques, i.e. coulometry, at a constant pH. The acid amount obtained in this way may be used as a measure for the vitality of the cells.

Following is a discussion of the subject matter of the invention, as represented by the examples shown in the attached drawings.

BRIEF DESCRIPTION OF THE DRAWINGS

FIG. 1 is a section through a sensor comprising a base provided with a group of electrodes, and a hollow space or cavity designed to receive a liquid, FIG. 2 is a view from above of the surface of the electrode-carrying base shown in FIG. 1, and a block diagram of an electronic measuring device, FIG. 3 shows a detail of a the sensor—marked III in FIG. 1— at an enlarged scale and with additional components, FIG. 4 is a view from above of a base carrying several groups of electrodes.

It should be noted that FIGS. 1 to 3 are schematic drawings which are not true to scale.

DETAILED DESCRIPTION OF THE PREFERRED EMBODIMENTS

A measuring device for use with electroanalytic, coulometric measurement processes for investigation of the metabolism of cells is provided with a sensor 50 configured as a container—or chamber-like part. The sensor 50 has a body 51 with a base 53. The base 53 is provided with an insulating part or substrate, which is formed by a plane, electrically insulating, quadrangular small plate 54 made of sapphire. On the surface constituting its upper plane face in FIG. 1 the plate 54 is provided with four electrodes as presented in FIG. 2, i.e., a pH measuring electrode 56, a control and/or proton exchange electrode 57, a reference electrode 58, and a counterelectrode 59. Each electrode is electrically connected to a strip conductor 56a, 57a, 58a, and 59a, respectively located on the plate. In the view from above presented in FIG. 2 the measuring electrode 56 has a circular region shaped as a full circle. The control and/or proton exchange electrode 57 encircles the measuring electrode 56 almost completely, apart from a gap for the passage of the strip conductor 56a. The control and/or proton exchange electrode 57 thus is approximately C-shaped, forming a circular ring which is broken by the above gap, and has a surface that is considerably larger than that of the measuring electrode 56. The surface of the control and/or proton exchange electrode 57 preferably is at least five times, and even seven to fifteen times as large as that of the pH measuring electrode 56. Compared to the electrode 57, each of the two electrodes 58, 59 forms a narrow, approximately semicircular arc running along part of the length of the exterior rim of the electrode 57. The four strip conductors run parallel to a section of the edge of the plate 54 forming one of its four sides.

The measuring electrode 56 and the control and/or proton exchange electrode 57, part of which latter is also shown in FIG. 3, each are provided with a metallic coating 65, which is directly applied on the plate 54 and consists of a vapor-deposited layer of pure iridium, and with a monocrystalline oxide layer 66 of iridium oxide on top of the coating 65. The strip conductors 56a and 57a are iridium layers connected with the metallic coatings of the electrodes 56 and 57. The reference electrode 58 is made of silver chloride and the corresponding strip conductor 58a of silver. The counterelectrode 59 and its strip conductor 59a consist of platinum.

Between the different electrodes and strip conductors narrow spaces or gaps are provided to separate them from one another. The edges of the metallic coatings 65 and oxide layers 66 constituting the electrodes 56, 57 are further provided with protective layers—one of which, i.e. 68, is shown in FIG. 3 next to the exterior edge of electrode 57—providing electrical insulation and a liquid-tight seal when an analysis is performed. The protective layers 68 may be made of vapor-deposited, pure, undoped silicon or silicon dioxide.

On the side of the base 53 carrying the electrodes a small plate 71 is provided, which has a through-hole 71a concentric with the group of electrodes 56, 57, 58, 59, whose diameter approximately equals the enveloping circle of the group of electrodes.

In addition, a cover 73 is provided which is also configured as a small plate and is placed on the side of plate 71 facing away from plate 54, and which has a projection 73a projecting into the hole 71a. Taken together, the plates 54, 71 and the cover 73 bound a cavity 75 formed by the hole 71a, which is sealed tightly against its environment and is used as a receptacle for cells and a liquid. The cover 73 has two passages which open into the cavity 75 between the edge of the projection 73a and the rim of the hole 71a, constituting an inlet 73b and an outlet 73c for the liquid.

The small plate 71 is electrically insulating and may be made of synthetic material, or of mineral glass. The cover 73 is made of plastic, for example. The plate 54 and the cover 73 are held together by detachable fastening means, such as clips. The plate 71 may be permanently attached to the plate 51 or the cover 73, or it may be removably fixed between the cover 71 and the plate 54 so as to be detachable from either. The plate 71 may be in contact with the exterior rim of electrodes 58, 59 (FIGS. 1 and 3), although it should not cover these electrodes entirely, so that all electrodes 56, 57, 58, 59 will be adjacent to the cavity 75. The part of the iridium strip conductor strip 56a lying inside the cavity as seen in the view from above, is covered against the cavity 75 by means of an insulating layer of vapor-deposited silicon, for instance. In addition to the circular region in the center of the other electrodes, the electrode 56 could have another region in connection with the circular region, which would be linear, extend as far as to the edge of the cavity 75, be provided with an iridium oxide layer, and would not have an insulating layer. It should be noted in this context that the thicknesses of the vapor-deposited electrodes in FIGS. 1 and 3 are exaggerated. To ensure that the cavity 75 is sealed tightly against its environment, it would be possible to add a layer of electrically insulating and elastically deformable sealing and insulating material in the area of the plate 54 surrounding the electrodes 58, 59 and covered by plate 71, and on top of the strip conductors as well as between them.

The measuring device carrying the sensor 50 is provided with an electronic measuring unit 77, whose block diagram is shown in FIG. 2. The strip conductors 56a, 57a, 58a, 59a are electrically connected to the measuring unit 77 with its electronic circuit elements, for example, by means of a plug-in connection. The measuring unit 77 is provided with a measuring amplifier 78, whose inputs are connected to the pH measuring electrode 56 and the reference electrode 58. The measuring unit 77 is further provided with an electrically-controlled current source 79, whose outputs are connected to the control and/or proton exchange electrode 57 and the counterelectrode 59. The measuring unit 77 further comprises a measuring and control circuit 80, which is provided with a digital processor, for example, and a display- and/or recording unit 81. The measuring and control circuit 80 is connected to an output of the measuring amplifier 78, a control input of the current source 79 and to the display- and/or recording unit 81.

Moreover, preparation and feeding means are provided for the purpose of preparing and conditioning a liquid and feeding it into the cavity 75. The preparation means may be designed to adjust a suitable pH value in the liquid, and to heat and/or cool the liquid to a desired temperature, and to generate certain gas partial pressures in the liquid, in particular, oxygen and/or carbon dioxide partial pressures. In addition, a heating and/or cooling unit as well as a temperature control unit are provided to maintain the sensor, and, above all, the liquid and the cells contained in the cavity 75 during an analysis, at a desired temperature. Means for dielectrophoresis also may be provided to influence the cell movement in the cavity 75 in such a way that the cells are attached and immobilized in defined regions of the boundary surfaces of the cavity 75. The means for dielectrophoresis may be provided with dielectrophoresis electrodes which have a number of projections with edges, corners and/or small curvature radii, and are located and provided with an alternating current generator such that they may generate an inhomogeneous, alternating electrical field in the cavity 75. The dielectrophoresis electrodes may be made up of metal layers which may be applied on a surface of the cover 73 adjacent to the cavity 75. As an alternative, the dielectrophoresis electrodes could be located on the side of the small plate 54 facing away from the cavity 75, in which case they would generate an alternating electrical field for dielectrophoresis in the cavity 75, by acting through the plate 54 and electrodes 56, 57, 58, 59 and/or through the gaps between them.

If the electrodes 56, 57, 58, 59 are brought into contact with a aqueous electrolytic liquid, the pH value may be determined electroanalytically, for instance, potentiometrically, with the use of the pH measuring electrode 56 and the reference electrode 58. The electric potential arising between the two electrodes, 56 and 58, is related more or less linearly to the pH value, at least within a pH range of 4 to 9, approximately the pH value increasing with a decrease in potential.

If between the control and/or proton exchange electrode 57 and the counterelectrode 59 an electric current is passed through the aqueous, electrolytic, proton-containing liquid, the iridium oxide of the electrode 57 may accept or release protons by redox reactions, depending on the direction of the current. Such reactions may be described in a simplified way by the formula

$$IrO_2 + H^+ + e^- \rightleftharpoons IrOOH$$

Depending on the function of the electrode 57, i.e., whether it is primarily intended as a proton donor or as a proton acceptor during measurement, it is possible prior to this measurement and subsequent to any previous measurement to reduce the iridium of the oxide layer 66 with an electric cathode current, or to oxidize it with an electric anode current, and to saturate the oxide layer with protons or deprotonize it in the course of this process. In this context the publication of Olthuis et al., which has been referred to before, should be noted.

The measuring device comprising the sensor 50 and the electronic measuring unit 77 may be used to determine the amount of acid released by living cells of the cell culture in the course of at least one metabolic process. For the purpose of measurement a sample of a suspension to be analyzed, which may contain a conditioned nutrient solution and cells suspended therein, is introduced into the cavity 75 through the inlet 73b, for instance. In addition to a quantity of water and one or more nutrients dissolved therein, the liquid may contain dissolved oxygen, depending on the type of analysis to be performed, while being free of carbon dioxide and carbonic acid upon entering the cavity 75. The suspension may be required to fill the cavity 75 completely. After introducing the suspension, the amount of protons released and/or dissociated by the cells during a certain measurement period may be determined coulometrically.

Coulometric measurement may start as soon as the liquid and the cells have been introduced. A waiting period could be added to prolong the time between the point when the cells enter the cavity 75 and the beginning of measurement, however, to permit the cells to attach themselves to a surface of at least one of the sensor components, which is adjacent to the cavity 75, so that the cells are immobilized. If means for dielectrophoresis are available, cell attachment may be controlled and accelerated by dielectrophoresis. If desired, the cavity 75 may be rinsed with an amount of fresh, conditioned liquid at the end of the waiting period and prior to the beginning of the measurement process itself, the rinsing liquid being drained from the cavity 75 through the outlet 73c. The rinsing process will contribute to the liquid having an accurately defined composition at the beginning of measurement, and in particular, an accurately defined content of dissolved gas.

The temperature of liquid and cells may be adjusted to the desired value before and during a measurement process. If required, the inlet 73b and the outlet 73c, or lines connected to the inlet and the outlet, may be closed off to ensure that the cavity 75 is entirely sealed against the ambient temperature.

In a coulometric measuring process the difference in potential between the pH measuring electrode 56 and the reference electrode 58, which gives a measure for the pH value of the nutrient liquid, is determined by means of the measuring and control circuit 80. The current source 79 generates a direct electric current flowing through the nutrient liquid between the control and/or proton exchange electrode 57 and the counterelectrode 59. This current may be uniform or made up of a pulse train, and is directed such that the control and/or proton exchange electrode 57 can accept protons from the nutrient liquid. The measuring and control circuit 80 will automatically control the current source 79 so as to ensure that the amount of protons accepted by the electrode 57 will compensate the amount of protons released by the cells, and that the instantaneous pH value of the nutrient liquid will equal a preset pH value that is adjusted with the use of manually-operated controls and is conducive to cell development. The measuring and control circuit 80 may temporarily reverse the current direction if required, which will lead to a temporary proton release by the electrode 57. For control purposes so-called "fuzzy" logic may be used. In addition, the measuring and control circuit 80 will measure and integrate the current flowing through the nutrient liquid between the control and/or proton exchange electrode 57 and the counterelectrode 59 during a given measurement period which may be set manually, for example. The total amount of charge passed through the nutrient liquid during the measuring period to maintain a constant pH is also determined with the use of the measuring and control circuit 80. In this way a measure is obtained for the amount of acid that is directly released into the liquid by the cells and/or is formed in the liquid. The display and/or recording unit 81 may then be used to display and/or record the amount of charge or a proportional quantity, and, if desired, the pH value.

After the end of a measurement process the cavity 75 may be rinsed with liquid in such a way that the cells will remain inside the cavity; the composition of the liquid, or the temperature, or some other parameter may be modified. Subsequent thereto another coulometric measurement may be performed.

Once analysis of the cells in the cavity 75 is completed the cavity 75 may be rinsed in such a way that the cells will be removed. If necessary, the cover 73 may be separated temporarily from the plate 54 for the purpose of cleaning the parts bounding the cavity 74, the control and/or proton exchange electrode 57 may be regenerated electrochemically, if required, and a new sample may be introduced into the cavity 75.

Before the nutrient liquid is introduced into the cavity 75 for measurement, a substance, for instance a drug or environmental poison, may be added to it in order to analyze its effect on the cells. In addition to the oxygen, or instead of it, some other gas may be dissolved in the nutrient liquid for the purpose of measurement. In this way the sensor 50 may be used as a small bioreactor in which cells may be cultivated and their metabolism analyzed.

The multiple sensor 90 shown in FIG. 4 comprises a body 91 with a supporting base 93. The main component of the supporting base 93 is a small plate 94 made of sapphire carrying several—in this instance four—electrode groups 95 and strip conductor groups 95a. Each electrode group 95 has four electrodes arranged in analogy to the electrodes 56, 57, 58, 59. Each strip conductor group 95a has four strip conductors, each of which is connected to an electrode. As is shown in FIG. 4 all strip conductors may end on one and the same side of the quadrangular plate 94. Together with a cover 97 corresponding to cover 73, and a small plate corresponding to plate 71 and not visible in this drawing, the small plate 94 bounds a cavity for each group of electrodes, which is designed to receive a liquid to be analyzed. The cover 97 may be provided with inlets and outlets opening into a corresponding cavity in analogy to inlet 73b and outlet 73c. Together with a measuring apparatus the multiple sensor 90 permits simultaneous measurement of several samples.

The measuring device of the invention may be modified in several respects. For example, the small plate 54 or 94 made of sapphire may be replaced by a small plate made of ceramics or by a component of a different shape.

In the sensor shown in FIG. 1 the inlet 73b and the outlet 73c may be omitted, so that the cavity 75 is sealed completely. A sample to be analyzed may be introduced with a pipette or the like into the cavity from which the cover 73 has been removed temporarily. The same applies for the multiple sensor 90 of FIG. 4. It is also possible to use a multiple sensor in which more than four, for instance 6 or 24, groups of electrodes are provided on one and the same electrically insulating, single-piece plate.

The covers 73, 97 and/or the supporting bases 53, 93 and electrodes of the sensors shown in FIGS. 1 and 4 could also be made of transparent material, which would permit further analysis of the cells provided in the sensors, i.e., by microscopic and/or optical methods of analysis.

In the variants described above the pH measuring electrode, the control electrode, the reference electrode and the counterelectrode are arranged so as to be separated from one another, and there is no direct electrical connection between them. In this way pH measurement and the generation and control of the current used for proton exchange may take place continuously and simultaneously, or intermittently and alternatingly.

It would, however, be acceptable to employ one and the same electrode as a reference electrode for pH measurement and a counterelectrode for generation of a current flowing through the liquid. In this instance pH measurement and the generation of current required for proton exchange are performed alternatingly, though a continuous, simultaneous pH measurement and current generation and control would also be possible.

We claim:

1. A device for analyzing the metabolism of cells bordering on a liquid comprising a pH sensing means for measuring the pH value of said liquid; a control electrode for proton exchange with said liquid, and a counterelectrode, for contact with said liquid; wherein said pH sensing means, said control electrode and said counterelectrode are electrically connected to electronic circuit elements; and wherein said circuit elements generate an electric current flowing through said liquid between said control electrode and said counterelectrode, measure said current or a variable associated therewith, and control said current as well as said proton exchange in such a way that the pH value, as measured by said pH sensing means, equals a desired preset value.

2. A device according to claim 1, wherein said pH sensing means is provided with a pH measuring electrode for contact with said liquid, said pH measuring electrode having an electric potential with respect to said liquid which is dependent on the pH value of said liquid.

3. A device according to claim 2, further comprising a supporting base with an electrically insulating part, wherein said pH measuring electrode, said control electrode, and said counterelectrode are provided with electrically conductive or semi-conductive layers applied on said electrically insulating part.

4. A device according to claim 3, wherein said control electrode encircles said pH measuring electrode almost completely, and wherein said counterelectrode is located outside of said control electrode.

5. A device according to claim 3, wherein at least one of said pH measuring electrode and said control electrode includes an oxide layer of at least one metal oxide for contact with said liquid.

6. A device according to claim 5, wherein said oxide layer consists of at least one oxide of at least one metal selected from the group consisting of iridium, palladium, zirconium, niobium, rhodium, tantalum, rhenium and platinum.

7. A device according to claim 6, wherein said oxide layer is monocrystalline.

8. A device according to claim 3, further comprising a reference electrode for contact with said liquid, wherein said reference electrode together with said pH measuring electrode is used for pH measurement, and wherein said reference electrode is also located on said electrically insulating part outside of said control electrode.

9. A device according to claim 8, wherein at least one of said pH measuring electrode and said control electrode is provided with an oxide layer of at least one metal oxide, which can be brought into contact with said liquid.

10. A device according to claim 8, including plate means which, together with said supporting base, bounds a cavity adjacent to said pH measuring electrode, control electrode, reference electrode and counterelectrode, said cavity being sealed tight against its environment.

11. A device according to claim 1, wherein said electronic circuit elements include means for measuring an amount of charge generating said electric current during a measurement period.

* * * * *